United States Patent
Suga

(10) Patent No.: US 11,083,420 B2
(45) Date of Patent: Aug. 10, 2021

(54) ROBOTIC OPERATING TABLE AND HYBRID OPERATING SYSTEM

(71) Applicant: MEDICAROID CORPORATION, Kobe (JP)

(72) Inventor: Kazunori Suga, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 261 days.

(21) Appl. No.: 15/855,834

(22) Filed: Dec. 27, 2017

(65) Prior Publication Data
US 2018/0177469 A1    Jun. 28, 2018

(30) Foreign Application Priority Data
Dec. 28, 2016    (JP) .............................. JP2016-255013

(51) Int. Cl.
| | |
|---|---|
| A61B 6/04 | (2006.01) |
| A61G 13/04 | (2006.01) |
| A61B 5/00 | (2006.01) |
| A61G 13/06 | (2006.01) |
| A61B 5/055 | (2006.01) |
| A61B 34/30 | (2016.01) |
| A61N 5/10 | (2006.01) |

(52) U.S. Cl.
CPC ............ *A61B 6/0407* (2013.01); *A61B 5/055* (2013.01); *A61B 5/704* (2013.01); *A61B 6/0487* (2020.08); *A61G 13/04* (2013.01); *A61G 13/06* (2013.01); *A61B 34/30* (2016.02); *A61G 2210/50* (2013.01); *A61N 5/1049* (2013.01)

(58) Field of Classification Search
CPC ..... A61B 6/0407; A61B 6/0457; A61B 5/704; A61B 5/0555; A61B 34/30; A61B 2090/376; A61B 2090/374; A61B 90/37; A61B 6/0442; A61G 13/06; A61G 13/04; A61G 2210/50; A61G 13/10; A61N 5/1049
USPC ............................................................ 5/601
See application file for complete search history.

(56) References Cited

U.S. PATENT DOCUMENTS

| | | | | |
|---|---|---|---|---|
| 5,149,074 A | * | 9/1992 | Jarin ........................ | A61B 6/04 5/601 |
| 5,410,767 A | * | 5/1995 | Barud ...................... | A61B 6/04 108/143 |
| 6,502,261 B1 | * | 1/2003 | Harwood ............... | A61G 13/02 5/611 |

(Continued)

FOREIGN PATENT DOCUMENTS

| | | |
|---|---|---|
| DE | 102006055165 A1 | 5/2008 |
| DE | 102013215119 A1 | 6/2014 |

(Continued)

*Primary Examiner* — Nicholas F Polito
*Assistant Examiner* — Luke Hall
(74) *Attorney, Agent, or Firm* — Metrolex IP Law Group, PLLC

(57) ABSTRACT

An operating table may include: a table on which to place a patient; a base fixed to a floor; and an articulated robotic arm including a first end supported on the base and a second end supporting the table at a position near the first end in a longitudinal direction of the table. The robotic arm may take a first posture in which the robotic arm is housed under the table when the table is situated at a first predetermined position. And a length of the robotic arm in the first posture in the longitudinal direction of the table is shorter than or equal to 1/2 of a length of the table in the longitudinal direction.

18 Claims, 6 Drawing Sheets

(56) References Cited

U.S. PATENT DOCUMENTS

| | | | | |
|---|---|---|---|---|
| 7,860,550 | B2* | 12/2010 | Saracen | A61B 6/548 |
| | | | | 600/410 |
| 8,126,114 | B2* | 2/2012 | Naylor | A61B 34/71 |
| | | | | 378/65 |
| 8,160,205 | B2 | 4/2012 | Saracen et al. | |
| 8,740,880 | B2* | 6/2014 | Pinault | A61N 5/1049 |
| | | | | 606/1 |
| 8,904,582 | B2* | 12/2014 | Bergfjord | A61G 13/06 |
| | | | | 5/601 |
| 9,326,907 | B2* | 5/2016 | Marie | A61B 6/4494 |
| 2004/0216232 | A1* | 11/2004 | Bradcovich | A61G 13/10 |
| | | | | 5/601 |
| 2005/0234327 | A1* | 10/2005 | Saracen | A61B 6/548 |
| | | | | 600/407 |
| 2008/0301872 | A1* | 12/2008 | Fahrig | A61B 6/5276 |
| | | | | 5/81.1 R |
| 2009/0003532 | A1* | 1/2009 | Weber | A61B 6/0487 |
| | | | | 378/209 |
| 2013/0336449 | A1* | 12/2013 | Tanabe | A61N 5/1067 |
| | | | | 378/62 |
| 2014/0034061 | A1* | 2/2014 | Marie | A61G 7/1057 |
| | | | | 128/845 |
| 2015/0059095 | A1* | 3/2015 | Bergfjord | A61N 5/1069 |
| | | | | 5/611 |
| 2015/0135438 | A1* | 5/2015 | Marugg | A61G 13/04 |
| | | | | 5/608 |
| 2015/0327818 | A1* | 11/2015 | Buck | A61G 13/04 |
| | | | | 5/608 |
| 2017/0156684 | A1* | 6/2017 | Van De Rijdt | A61B 6/04 |
| 2018/0085603 | A1* | 3/2018 | Kruesi | A61N 5/1049 |

FOREIGN PATENT DOCUMENTS

| | | |
|---|---|---|
| JP | 2006-239794 A | 9/2006 |
| JP | 2008-539963 A | 11/2008 |
| JP | 2009-131718 A | 6/2009 |
| JP | 2009-142970 A | 7/2009 |
| JP | 2014-000128 A | 1/2014 |

* cited by examiner

ROBOTIC OPERATING TABLE AND HYBRID OPERATING SYSTEM

CROSS REFERENCE TO RELATED APPLICATIONS

This application claims priority based on 35 USC 119 from prior Japanese Patent Application No. 2016-255013 filed on Dec. 28, 2016, entitled "ROBOTIC OPERATING TABLE AND HYBRID OPERATING ROOM", the entire contents of which are incorporated herein by reference.

BACKGROUND

This disclosure relates to a robotic operating table and a hybrid operating system.

A patient positioning assembly has heretofore been known which uses a robotic arm to move a table with a patient placed thereon and position the patient relative to a treatment radiation source (see Japanese Patent Application Publication No. 2009-131718 (Patent Literature 1), for example).

Meanwhile, there has heretofore been a demand for an operating table that allows a table with a patient placed thereon to be easily moved while preventing interference with surrounding equipment in an operating room. To this end, one may consider applying the patient positioning assembly of Patent Literature 1 mentioned above to an operating table in an operating room to move the table with a patient placed thereon by using the robotic arm. In this way, the table with the patient placed thereon can be easily moved while being prevented from interfering with surrounding equipment, unlike cases where an operating table is moved using casters.

SUMMARY

Since patient positioning assemblies as described in Patent Literature 1 mentioned above are intended for irradiation of the patient with treatment radiation, they do not need to consider situations where staff work for a long time around the table with the patient placed thereon, and typically use a large robotic arm. For this reason, if applied to an operating table, the robotic arm of Patent Literature 1 reduces the space around the operating table and may interfere with medical personnel during surgical operations. Also, in a hybrid operating room, radiography and a surgical operation on cerebral blood vessels are often performed at an imaging position and a surgical operation position that are close to each other. In this case, for the imaging position, it is necessary to leave a space under the table place a C-arm to which an X-ray irradiation part and an X-ray detection part are connected. For the surgical operation position, which is close to the imaging position, it is necessary to leave a sufficient space around the table for the medical personnel.

One or more embodiments of a robotic operating table and a hybrid operating system is capable of leaving a sufficient space under a table on which to place a patient and of leaving a sufficient space around the table. Moreover, one or more embodiments provide a robotic operating table and a hybrid operating system capable of leaving a space under a table for radiography and leaving a space around the table for a surgical operation even in a case where the imaging position for the radiography and the surgical operation position are close to each other.

A robotic operating table according to a first aspect of one or more embodiments includes a table on which to place a patient; a base buried or fixed to a floor; and an articulated robotic arm including a first end supported on the base and a second end supporting the table. The articulated robotic arm supports the table at a position near a first end in the longitudinal direction of the table. The articulated robotic arm is capable of assuming a posture in which the robotic arm is housed under the table when the table is situated at a predetermined position. A length of the robotic arm in the posture in the longitudinal direction of the table is shorter than or equal to ½ of the length of the table in the longitudinal direction.

A robotic operating table according to a second aspect of one or more embodiments includes a table on which to place a patient; a base buried or fixed to a floor; and an articulated robotic arm including a first end supported on the base and a second end supporting the table at a position near a first end in a longitudinal direction of the table. The articulated robotic arm assumes a posture in which the robotic arm is housed under the table when the table is situated at a predetermined position. When the robotic arm is in the posture, a length of the robotic arm in the longitudinal direction of the table is shorter than or equal to ½ of a length of the table in the longitudinal direction. When translationally moving the table in the longitudinal direction of the table from the predetermined position, the robotic arm translationally moves the table without sticking out from the table in a transverse direction of the table.

A hybrid operating system according to a third aspect of one or more embodiments include at least one imaging apparatus selected from a radiographic imaging apparatus that captures a radiographic projection image of a patient and a magnetic resonance imaging apparatus that captures a magnetic resonance image of a patient; and an operating table including a table on which to place a patient, a base buried or fixed to a floor, and an articulated robotic arm including a first end supported on the base and a second end supporting the table at a position near a first end in a longitudinal direction of the table. The robotic arm assumes a posture in which the robotic arm is housed under the table when the table is situated at a predetermined position. A length of the robotic arm in the posture in the longitudinal direction of the table is shorter than or equal to ½ of a length of the table in the longitudinal direction.

BRIEF DESCRIPTION OF DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
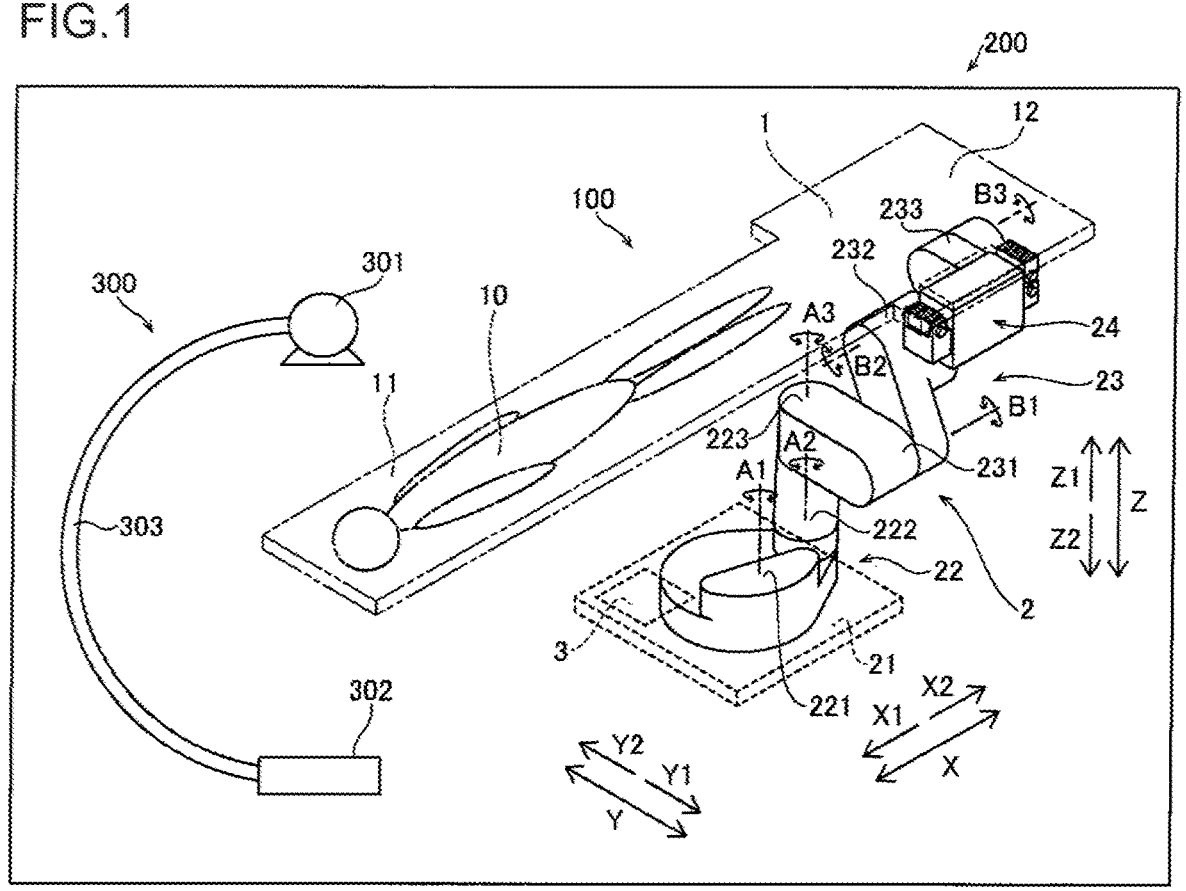
FIG. 1 is a view illustrating an overview of a hybrid operating system including a robotic operating table according to one or more embodiments.

Embodiments are described with reference to drawings, in which the same constituents are designated by the same reference numerals and duplicate explanation concerning the same constituents may be omitted for brevity and ease of explanation. The drawings are illustrative and exemplary in nature and provided to facilitate understanding of the illustrated embodiments and may not be exhaustive or limiting. Dimensions or proportions in the drawings are not intended to impose restrictions on the disclosed embodiments. For this reason, specific dimensions and the like should be interpreted with the accompanying descriptions taken into consideration. In addition, the drawings include parts whose dimensional relationship and ratios are different from one drawing to another.

Prepositions, such as "on", "over" and "above" may be defined with respect to a surface, for example a layer surface, regardless of the orientation of the surface in space.

(Configuration of Robotic Operating Table)

An overview of a robotic operating table 100 according to an embodiment is explained with reference to FIG. 1 to FIG. 13.

As illustrated in FIG. 1, the robotic operating table 100 is provided in a hybrid operating system 200. The hybrid operating system 200 is provided with a radiographic imaging apparatus 300 that captures a radiographic projection images of a patient 10. The robotic operating table 100 is used as a table for operations performed in a setting such as a surgery or internal medicine setting. The robotic operating table 100 is capable of moving a table 1 to a placement position at which to place the patient 10 onto the table 1, and moving the patient 10 to an anesthetization position, a surgical operation position, an examination position, a treatment position, a radiographic imaging position, and so on while the patient 10 is placed on the table 1. Also, the robotic operating table 100 is capable of tilting the patient 10 while the patient 10 is placed on the table 1.

The robotic operating table 100 includes the table 1, on which to place the patient, an articulated robotic arm 2, and a control unit 3. The table 1 includes a radiolucent part 11 and a support part 12 supporting the radiolucent part 11. The articulated robotic arm 2 includes a base 21, a horizontal articulated assembly 22, a vertical articulated assembly 23, and a pitch mechanism 24. The horizontal articulated assembly 22 includes horizontal joints 221, 222, and 223. The vertical articulated assembly 23 includes vertical joints 231, 232, and 233. The radiographic imaging apparatus 300 includes an X-ray irradiation part 301, an X-ray detection part 302, and a C-arm 303.

Figure 2:
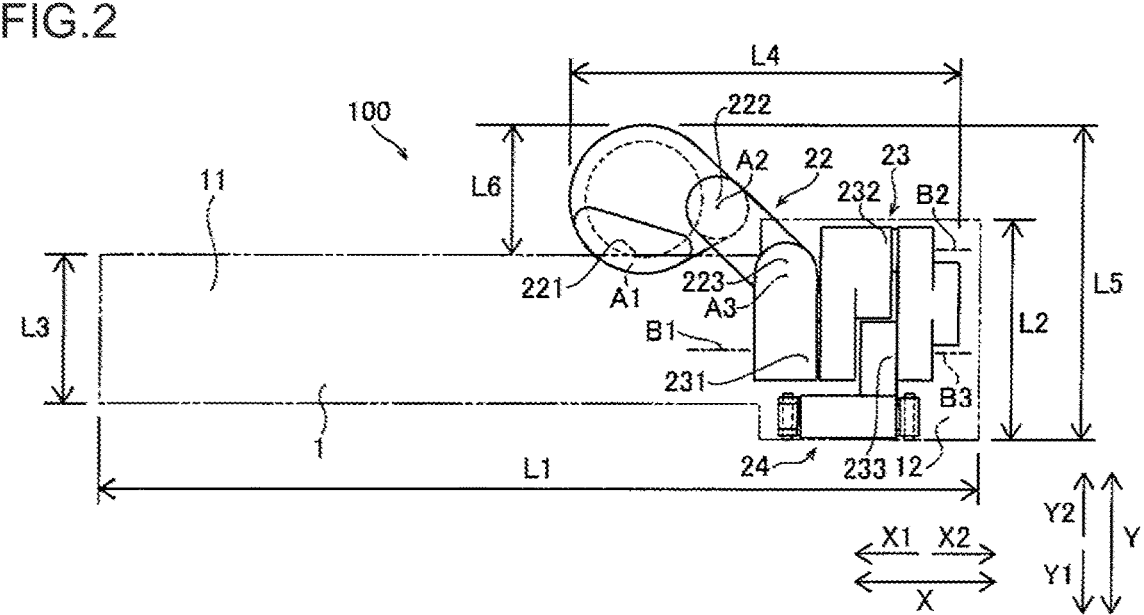
FIG. 2 is a plan view illustrating the robotic operating table in a second posture according to one or more embodiments.

As illustrated in FIG. 1, the table 1 is formed in the shape of a substantially rectangular flat plate. Also, the upper surface of the table 1 is formed to be substantially flat. The table 1 has its longitudinal direction along an X direction and its transverse direction along a Y direction. Note that, while the table 1 is rotatable about an axis along the vertical direction (Z direction), the horizontal direction along the longitudinal direction of the table 1 is defined as the X direction and the horizontal direction along the transverse direction of the table 1 is defined as the Y direction here. In other words, the X direction and the Y direction represent directions based on the table 1. As illustrated in FIG. 2, the table 1 has a length L1 in the longitudinal direction (X direction). Also, the support part 12 on the X2 direction side of the table 1 has a length L2 in the transverse direction (Y direction). Moreover, the radiolucent part 11 on the X1 direction side of the table 1 has a length L3 shorter than L2 in the transverse direction (Y direction). For example, L1 is 2800 mm, L2 is 740 mm, and L3 is 500 mm. Note that, preferably, L1 is set to be longer than or equal to 2000 mm but shorter than or equal to 3000 mm, L2 is set to be longer than or equal to 500 mm but shorter than or equal to 800 mm, and L3 is set to be longer than or equal to 500 mm but shorter than or equal to 800 mm. L3 is more preferably longer than or equal to 500 mm but shorter than or equal to 700 mm.

As illustrated in FIG. 1, the patient 10 is placed on the radiolucent part 11 of the table 1. The radiolucent part 11 is disposed on the X1 direction side. The radiolucent part 11 is formed in a substantially rectangular shape. The radiolucent part 11 is made of a radiolucent material. The radiolucent part 11 is made of a carbon material (graphite), for example. The radiolucent part 11 is made of a carbon fiber reinforced plastic (CFRP), for example. In this way, a radiographic image of the patient 10 can be captured while the patient 10 is placed on the radiolucent part 11.

The support part 12 of the table 1 is connected to the articulated robotic arm 2. The support part 12 is disposed on the X2 direction side. The support part 12 is formed in a substantially rectangular shape. The support part 12 supports the radiolucent part 11. The support part 12 is made of a material smaller in radiolucency than the radiolucent part 11. The support part 12 is made of metal, for example. The support part 12 is made of a steel material or an aluminum material, for example.

The table 1 is moved by the articulated robotic arm 2. Specifically, the table 1 is movable in the X direction, which is a horizontal direction, in the Y direction, which is the horizontal direction perpendicular to the X direction, and in the Z direction, which is perpendicular to the X direction and the Y direction and is the vertical direction. Moreover, the table 1 is rotatable (capable of being caused to roll) about an axis along the X direction. The table 1 is also rotatable (capable of being caused to pitch) about an axis along the Y direction. The table 1 is also rotatable (capable of being caused to yaw) about an axis along the Z direction.

The articulated robotic arm 2 moves the table 1. As illustrated in FIG. 1, one end of the articulated robotic arm 2 is supported on the base 21, which is fixed to the floor, while the opposite end supports the table 1 such that the articulated robotic arm 2 can move the table 1. Specifically, the articulated robotic arm 2 is supported on the base 21 such that the articulated robotic arm 2 is rotatable about an axis along the vertical direction (Z direction). Also, the articulated robotic arm 2 supports the table 1 at a position near its one end on the X2 direction side in the longitudinal direction (X direction). In other words, the opposite end of the articulated robotic arm 2 supports the support part 12, which is situated on the one end side of the table 1.

The articulated robotic arm 2 moves the table 1 with seven degrees of freedom. Specifically, with the horizontal articulated assembly 22, the articulated robotic arm 2 has three degrees of freedom to rotate about a vertical rotation axis A1, rotate about a vertical rotation axis A2, and rotate about a vertical rotation axis A3. Further, with the vertical articulated assembly 23, the articulated robotic arm 2 has three degrees of freedom to rotate about a horizontal rotation axis B1, rotate about a horizontal rotation axis B2, and rotate about a horizontal rotation axis B3. Furthermore, with the pitch mechanism 24, the articulated robotic arm 2 has one degree of freedom to allow the table 1 to pitch about a rotation axis along its transverse direction (Y direction) (see FIG. 12 and FIG. 13).

The base 21 is buried in and fixed to the floor. The base 21 is provided substantially at the center of the range of movement of the table 1 in a plan view (as seen from the Z direction).

One end of the horizontal articulated assembly 22 is supported on the base 21. Moreover, the opposite end of the horizontal articulated assembly 22 supports one end of the vertical articulated assembly 23. The horizontal joint 221 of the horizontal articulated assembly 22 rotates about the rotation axis A1 along the Z-direction. The horizontal joint 222 of the horizontal articulated assembly 22 rotates about the rotation axis A2 along the Z-direction. The horizontal joint 223 of the horizontal articulated assembly 22 rotates about the rotation axis A3 along the Z-direction.

The one end of the vertical articulated assembly 23 is supported on the horizontal articulated assembly 22. Moreover, the opposite end of the vertical articulated assembly 23 supports the pitch mechanism 24. The vertical joint 231 of the vertical articulated assembly 23 rotates about the rotation axis B1 along the X-direction. The vertical joint 232 of the vertical articulated assembly 23 rotates about the rotation axis B2 along the X-direction. The vertical joint 233 of the vertical articulated assembly 23 rotates about the rotation axis B3 along the X-direction.

The distance between each pair of adjacent joints has a length shorter than the length of the table 1 in the transverse direction (Y direction). Specifically, the distance between the rotation axis A1 and the rotation axis A2, the distance between the rotation axis A2 and the rotation axis A3, the distance between the rotation axis A3 and the rotation axis B1, the distance between the rotation axis B1 and the rotation axis B2, and the distance between the rotation axis B2 and the rotation axis B3 each have a length shorter than the length L3 of the table 1 in the transverse direction.

The horizontal joints 221 to 223 and the vertical joints 231 to 233 each include a servomotor (not illustrated), a reducer (not illustrated) that reduces speed of the rotation from the servomotor and transmits the reduced-speed rotation, and an electromagnetic brake. The horizontal joints 221 to 223 and the vertical joints 231 to 233 are each rotated about the corresponding rotation axis by driving the servomotor.

Here, in this embodiment, as illustrated in FIG. 3 to FIG. 6, the articulated robotic arm 2 is capable of assuming a first posture in which its length in the direction parallel to the longitudinal direction of the table 1 (X direction) is shorter than or equal to ½ of the length of the table 1 in the longitudinal direction. Specifically, the length of the articulated robotic arm 2 in the first posture in the direction parallel to the longitudinal direction of the table 1 (X direction) is shorter than or equal to ½ of the length of the table 1 in the longitudinal direction, and the articulated robotic arm 2 in the first posture is disposed within a space between the opposite transverse ends of the table 1 in the direction parallel to the transverse direction of the table 1 (Y direction).

Figure 3:
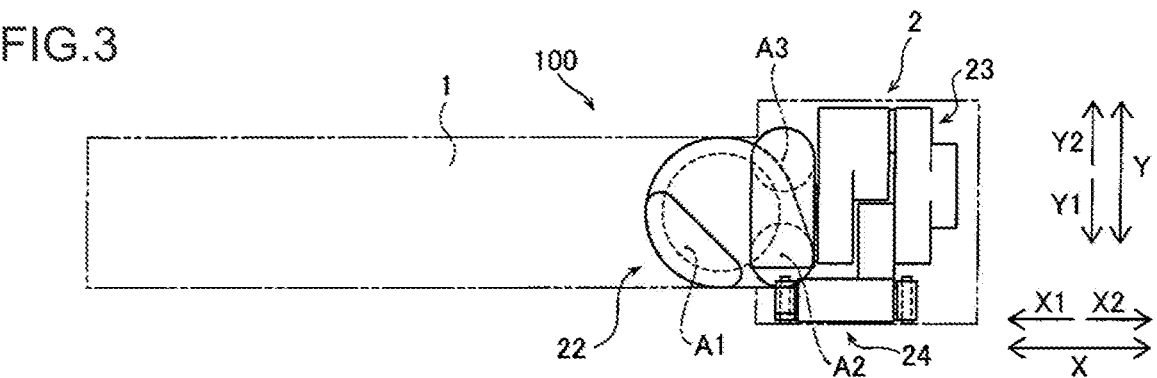
FIG. 3 is a plan view illustrating a first example of the robotic operating table in a first posture according to one or more embodiments.
Figure 4:
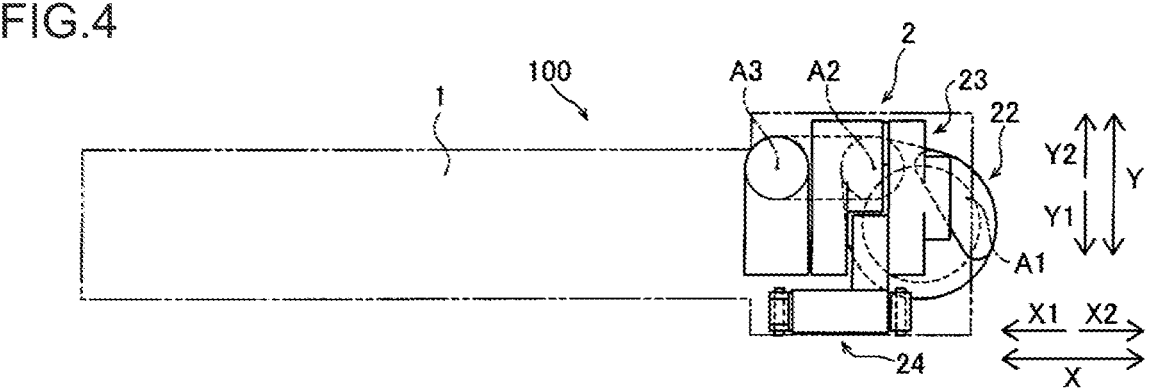
FIG. 4 is a plan view illustrating a second example of the robotic operating table in the first posture according one or more embodiments.
Figure 5:
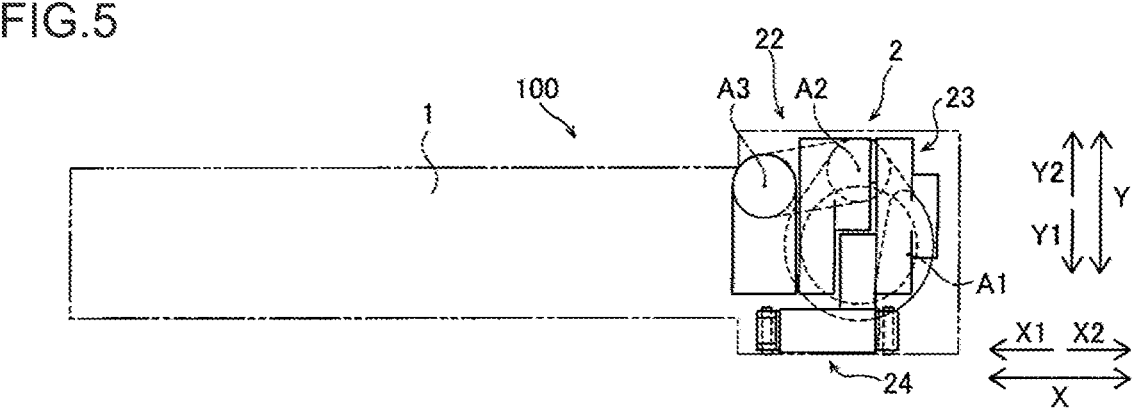
FIG. 5 is a plan view illustrating a third example of the robotic operating table in the first posture according to one or more embodiments.
Figure 6:
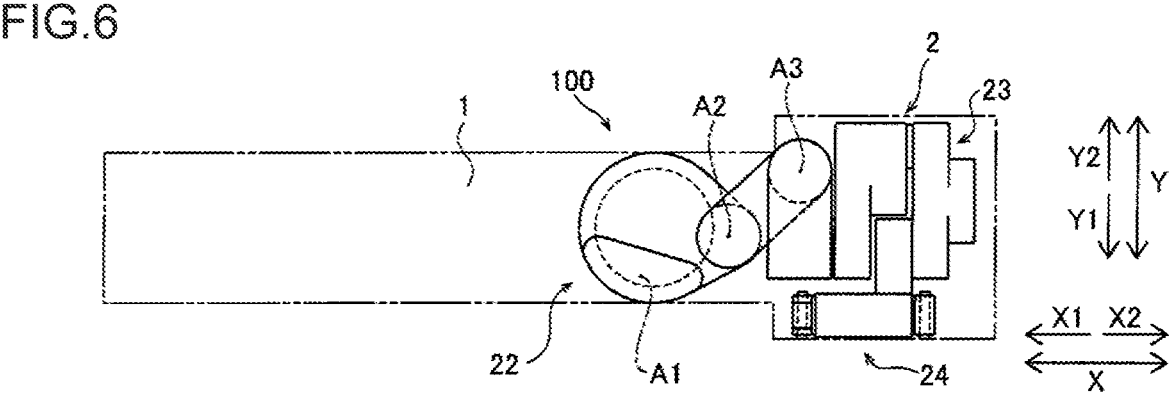
FIG. 6 is a plan view illustrating a fourth example of the robotic operating table in the first posture according to the one embodiment.

FIG. 3 illustrates the articulated robotic arm 2 in the first posture in a state where the articulated robotic arm 2 has positioned the table 1 to a reference position. FIG. 4 illustrates the articulated robotic arm 2 in the first posture in a state where the articulated robotic arm 2 has fully moved the table 1 in the horizontal X1 direction from the reference position. FIG. 5 illustrates a state where the horizontal articulated assembly 22 and the vertical articulated assembly 23 completely lie over one another in the plan view (as seen from the Z direction) such that the length of the articulated robotic arm 2 in the first posture in the direction parallel to the longitudinal direction of the table 1 (X direction) is minimum. FIG. 6 illustrates the articulated robotic arm 2 in the first posture in a state where the articulated robotic arm 2 has fully moved the table 1 in the horizontal X2 direction from the reference position.

As illustrates in FIG. 3, FIG. 5, and FIG. 6, the articulated robotic arm 2 in the first posture is preferably disposed to be entirely hidden under the table 1 in the plan view (as seen from the Z direction). For example, the articulated robotic arm 2 assumes the first posture to be housed in a housing space which is a space under the table 1 when the table 1 is positioned at a surgical operation position. Specifically, the articulated robotic arm 2 is folded and completely hidden under the table 1 in the plan view (as seen from the Z direction) in a state where the articulated robotic arm 2 has moved the table 1 to a position at which to perform a surgical operation or treatment on the patient 10 placed on the table 1. Note that the length of the articulated robotic arm 2 in the first posture in the direction parallel to the longitudinal direction of the table 1 (X direction) is preferably shorter than or equal to ⅖ of the length of the table 1 in the longitudinal direction in view of leaving a certain space under the table 1. Moreover, the length of the articulated robotic arm 2 in the first posture in the direction parallel to the longitudinal direction of the table 1 (X direction) is preferably shorter than or equal to ¼ of the length of the table 1 in the longitudinal direction in view of the strength of the articulated robotic arm 2.

Also, as illustrated in FIG. 2, in this embodiment, the articulated robotic arm 2 is capable of assuming a second posture different from the first posture in the plan view (as seen from the Z direction). The length of the articulated robotic arm 2 in the second posture in the direction parallel to the longitudinal direction of the table 1 (X direction) is shorter than or equal to ½ of the length of the table 1 in the longitudinal direction, and the length of the portion of the articulated robotic arm 2 sticking out from the table 1 in the direction parallel to the transverse direction of the table 1 (Y direction) is shorter than or equal to the length of the table 1 in the transverse direction in the plan view (as seen from the Z direction).

In the example illustrated in FIG. 2, the articulated robotic arm 2 has a length L4 in the X direction and a length L5 in the Y direction. The length L4 is shorter than or equal to the length L1 of the table 1 in the X direction. Also, the length L5 is shorter than or equal to a length twice longer than the length L2 of the table 1 in the Y direction. In the example illustrated in FIG. 2, the articulated robotic arm 2 sticks out from the table 1 by a length L6 in the X direction. The length L6 is shorter than or equal to the length L2 of the table 1 in the Y direction. Moreover, the length L6 is shorter than or equal to the length L3 of the table 1 in the Y direction.

The articulated robotic arm 2 translationally moves the table 1 from the first posture or the second posture by using the horizontal articulated assembly 22 while maintaining its length in the direction parallel to the transverse direction of the table 1 (Y direction). In the examples illustrated in FIG. 3 to FIG. 6, the articulated robotic arm 2 moves the table 1 in the X direction. In these examples, the articulated robotic arm 2 translates the table 1 by driving the horizontal articulated assembly 22 such that the articulated robotic arm 2 remains within the space between the opposite ends of the table 1 in the Y direction.

The articulated robotic arm 2 moves the table 1 in the vertical direction (Z direction) by using the vertical articulated assembly 23 while maintaining the first posture or the second posture. Specifically, the vertical articulated assembly 23 is disposed to be completely hidden under the table 1 in the plan view regardless of the posture. Hence, when only the vertical articulated assembly 23 is driven, the articulated robotic arm 2 can move the table 1 in the vertical direction while maintaining the first posture or the second posture. Note that the articulated robotic arm 2 in this embodiment can lower the table 1 down to a height of 500 mm while maintaining the first posture or the second posture. In this way, the robotic operating table 100 can handle surgical operations which medical personnel perform while sitting on chairs. Moreover, the articulated robotic arm 2 can raise the table 1 up to a height of 1100 mm while maintaining the first posture or the second posture.

Figure 7:
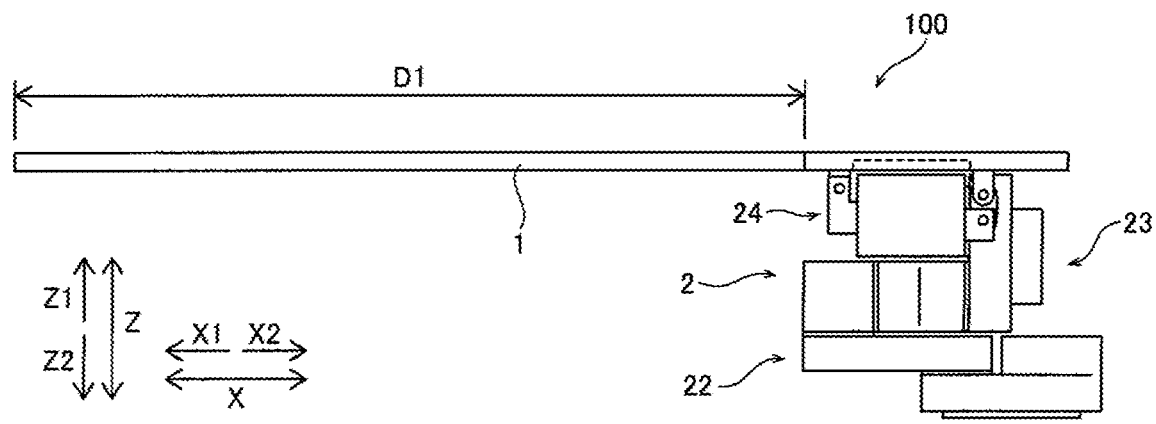
FIG. 7 is a side view for explaining the maximum imageable range in the second example of the robotic operating table according one or more embodiments.
Figure 8:
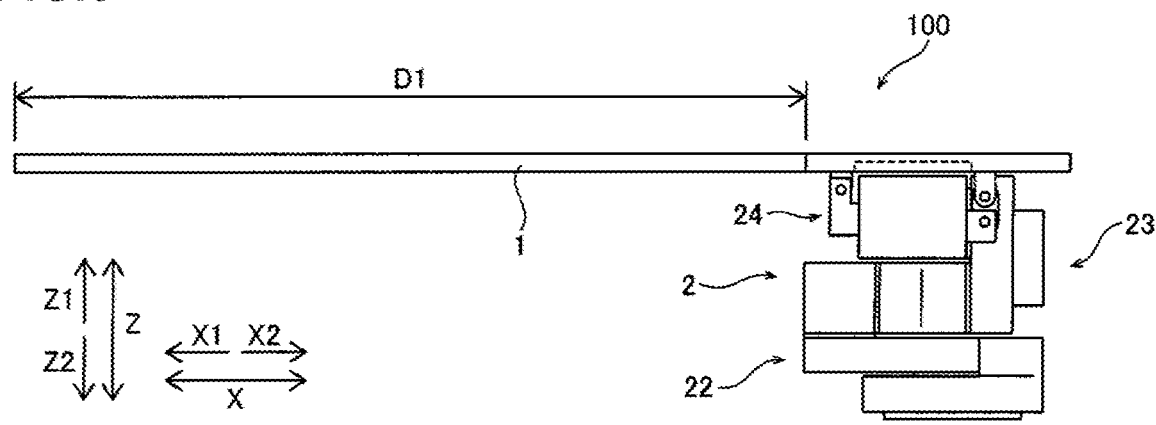
FIG. 8 is a side view for explaining the maximum imageable range in the third example of the robotic operating table according to one or more embodiments.

FIG. 7 is a side view of the articulated robotic arm 2 in FIG. 4, and FIG. 8 is a side view of the articulated robotic arm 2 in FIG. 5. As illustrated in FIG. 7 and FIG. 8, in this embodiment, the radiographic imaging apparatus 300 can capture an image over a distance D1 in the X direction as its maximum imageable range with the articulated robotic arm 2 disposed folded on the X2 side of the table 1. In other words, with the articulated robotic arm 2 disposed folded on the X2 side of the table 1, a space covering the distance D1 in the X direction is left under the table 1. The distance D1 is substantially equal to the length of the radiolucent part 11 in the X direction, for example. In other words, with the robotic operating table 100 in this embodiment, the radiographic imaging apparatus 300 can capture an image of substantially the whole body of the patient 10.

Figure 9:
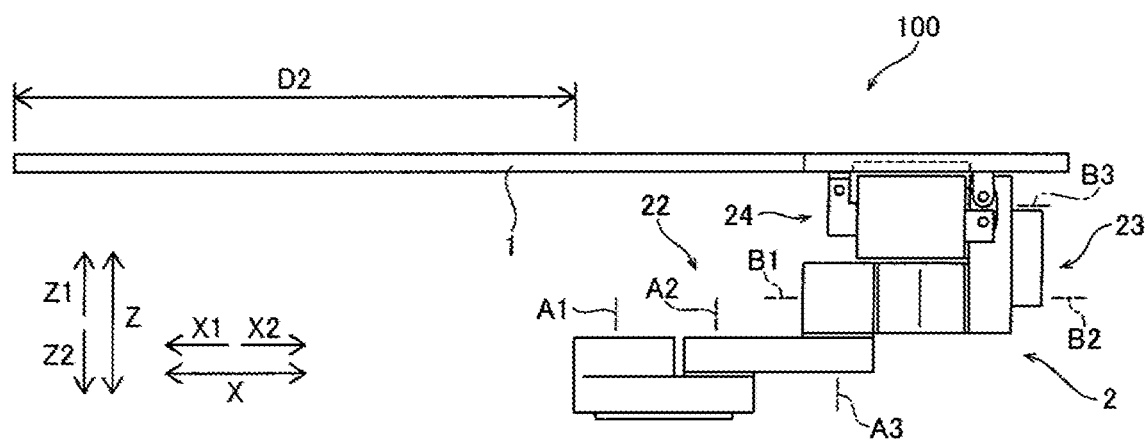
FIG. 9 is a side view for explaining the minimum imageable range in the fourth example of the robotic operating table according to one or more embodiments.

FIG. 9 is a side view of the articulated robotic arm 2 in FIG. 6. As illustrated in FIG. 9, in this embodiment, the radiographic imaging apparatus 300 can capture an image over a distance D2 in the X direction as its minimum imageable range with the articulated robotic arm 2 fully extended in the horizontal X2 direction. In other words, with the articulated robotic arm 2 fully extended in the horizontal X2 direction, a space covering the distance D2 in the X direction is left under the table 1. The distance D2 is longer than or equal to ½ of the length of the radiolucent part 11 in the X direction, for example. In other words, with the robotic operating table 100 in this embodiment, the radiographic imaging apparatus 300 can capture an image of at least half of the whole body of the patient 10. In this embodiment, D1 is 1800 mm and D2 is 1540 mm, for example.

Also, in this embodiment, the articulated robotic arm 2 causes the table 1 to yaw about an axis along the vertical direction (Z direction) by using at least one of the horizontal joints (at least one of 221, 222, and 223). For example, the articulated robotic arm 2 causes the table 1 to yaw by using the bottom horizontal joint 221 or the top horizontal joint 223. Alternatively, the articulated robotic arm 2 may cause the table 1 to yaw by driving two or all of the horizontal joints in conjunction with each other.

Figure 10:
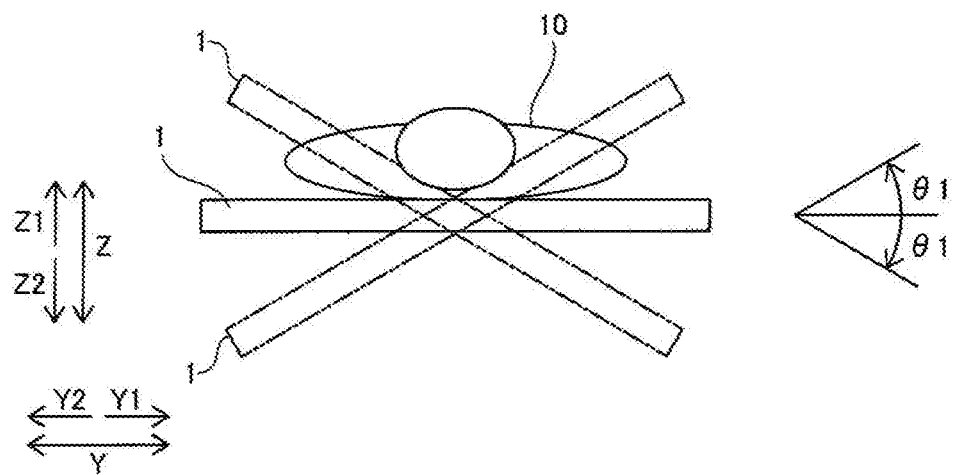
FIG. 10 is a front view for explaining roll of the robotic operating table according to one or more embodiments.

Also, as illustrated in FIG. 10, the articulated robotic arm 2 causes the table 1 to roll about an axis along the longitudinal direction (X direction) by using at least one of the vertical joints (at least one of 231, 232, and 233). For example, the articulated robotic arm 2 causes the table 1 to roll by using the bottom vertical joint 231 or the top vertical joint 233. Alternatively, the articulated robotic arm 2 may cause the table 1 to roll by driving two or all of the vertical joints in conjunction with each other. In a view of the table 1 from the X direction, the articulated robotic arm 2 is capable of causing the table 1 to roll up to an angle θ1 clockwise with respect the horizontal direction and causing the table 1 to roll up to the angle θ1 counterclockwise with respect the horizontal direction. θ1 is 30 degrees, for example.

Figure 11:
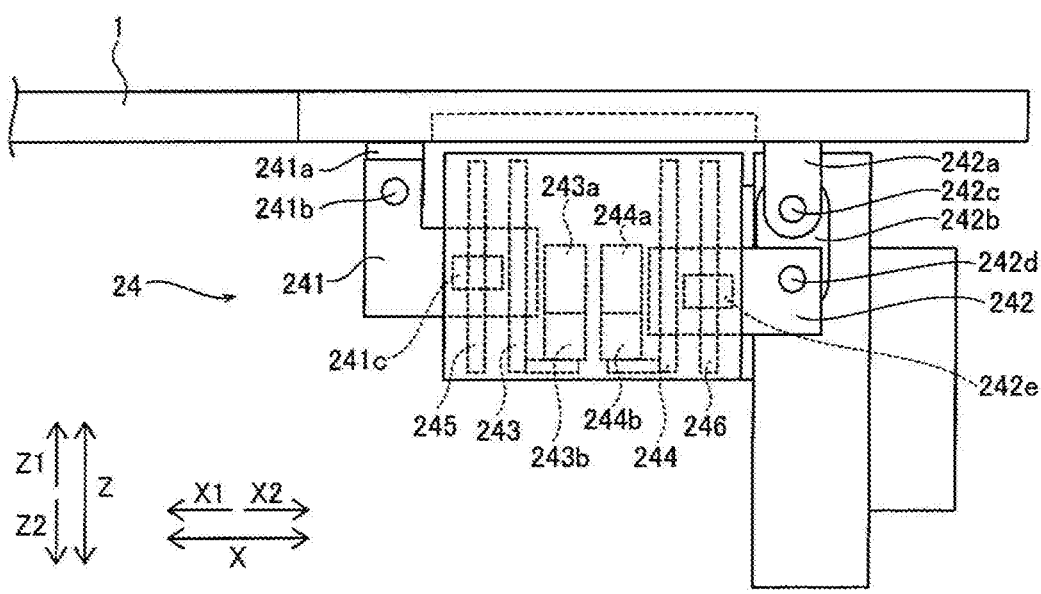
FIG. 11 is a side view illustrating a pitch mechanism of the robotic operating table according to one or more embodiments.
Figure 12:
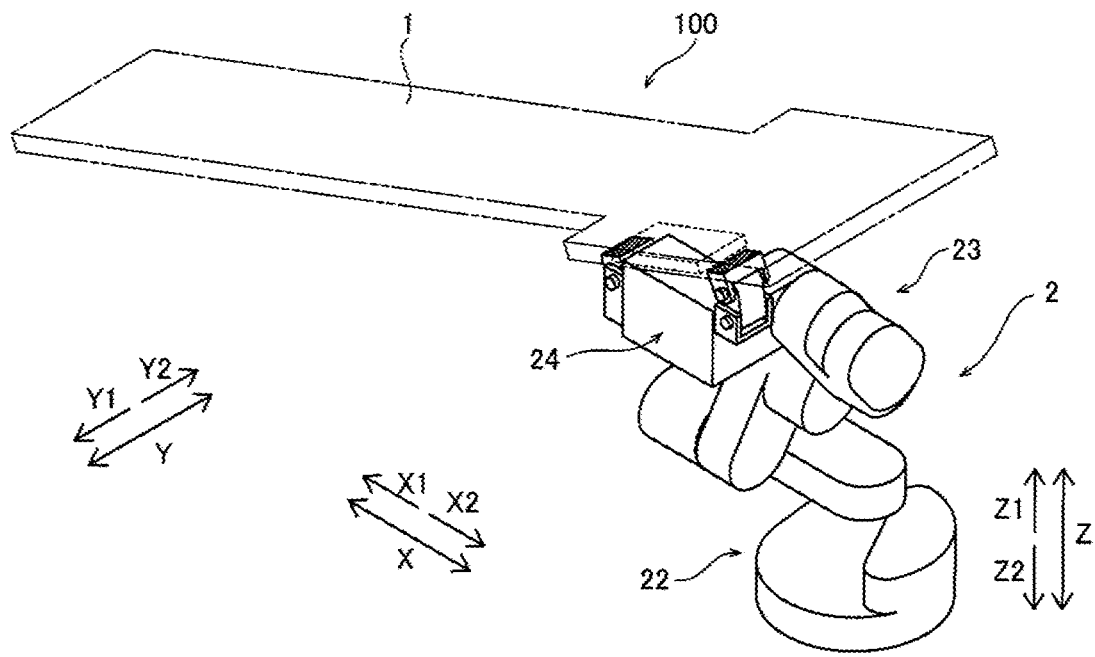
FIG. 12 is a perspective view for explaining pitch of the robotic operating table according to one or more embodiments.
Figure 13:
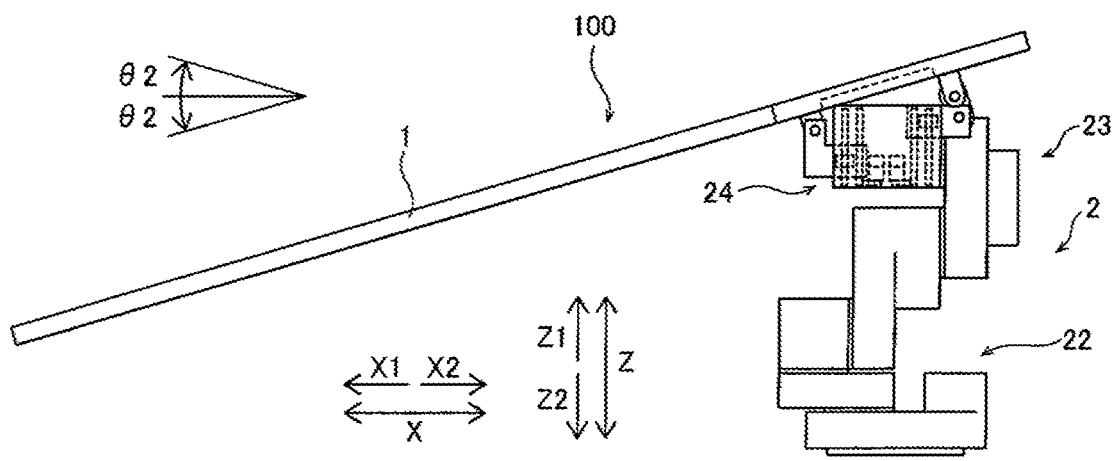
FIG. 13 is a side view for explaining the pitch of the robotic operating table according to one or more embodiments.

Also, as illustrated in FIG. 12 and FIG. 13, the articulated robotic arm 2 causes the table 1 to pitch about an axis along the transverse direction (Y direction) by using the pitch mechanism 24. As illustrated in FIG. 11, the pitch mechanism 24 includes a first support member 241, a second support member 242, a first ball screw 243, a second ball screw 244, a first linear guide 245, and a second linear guide 246. The first support member 241 includes a coupling part 241a, a pivot shaft 241b, and a slider 241c. The second support member 242 includes coupling parts 242a and 242b, pivot shafts 242c and 242d, and a slider 242e. The first ball screw 243 is connected to a motor 243a through a reducer 243b. The second ball screw 244 is connected to a motor 244a through a reducer 244b.

The pitch mechanism 24 is supported on the opposite end of the vertical articulated assembly 23. The pitch mechanism 24 is connected to the table 1 and supports the table 1 such that the table 1 can pitch. Specifically, the pitch mechanism 24 supports the table 1 such that the table 1 can pitch by using the first support member 241 and the second support member 242. The first support member 241 and the second support member 242 are disposed away from each other by a predetermined distance along the direction parallel to the longitudinal direction of the table 1 (X direction). The first support member 241 is disposed on the X1 direction side. The second support member 242 is disposed on the X2 direction side. Moreover, the pitch mechanism 24 is disposed near one side of the table 1 in the transverse direction (Y direction). Specifically, the pitch mechanism 24 is disposed near the end of the table 1 in the Y1 direction.

The coupling part 241a of the first support member 241 is fixed to the table 1 and pivotally supported on the pivot shaft 241b. The first support member 241 is moved in the vertical direction (Z direction) by driving the first ball screw 243. Moreover, the first support member 241 is slidably mounted on the first linear guide 245. Specifically, the slider 241c, which is fixed to the first support member 241, is engaged with the first linear guide 245 to guide vertical movement of the first support member 241.

The coupling part 242a of the second support member 242 is fixed to the table 1 and pivotally supported on the pivot shaft 242c. The coupling part 242b is pivotally mounted on the pivot shafts 242c and 242d. The second support member 242 is moved in the vertical direction (Z direction) by driving the second ball screw 244. Moreover, the second support member 242 is slidably mounted on the second linear guide 246. Specifically, the slider 242e, which is fixed to the second support member 242, is engaged with the second linear guide 246 to guide vertical movement of the second support member 242.

The first ball screw 243 is disposed such that its shaft extends in the vertical direction (Z direction). The first ball screw 243 is engaged with the first support member 241. By driving the motor 243a, the first ball screw 243 is rotated and moves the first support member 241 in the vertical direction.

The second ball screw 244 is disposed such that its shaft extends in the vertical direction (Z direction). The second ball screw 244 is engaged with the second support member 242. By driving the motor 244a, the second ball screw 244 is rotated and moves the second support member 242 in the vertical direction.

The first linear guide 245 is disposed to extend in a direction substantially parallel to the direction of extension of the first ball screw 243. In other words, the first linear guide 245 is disposed to extend in the vertical direction (Z direction). The first linear guide 245 guides vertical movement of the first support member 241 through the slider 241c.

The second linear guide 246 is disposed to extend in a direction substantially parallel to the direction of extension of the second ball screw 244. In other words, the second linear guide 246 is disposed to extend in the vertical direction (Z direction). The second linear guide 246 guides vertical movement of the second support member 242 through the slider 242e.

As the first support member 241 is moved to a position lower than the second support member 242, the table 1 is caused to pitch such that its X1 side becomes lower. In contrast, as the first support member 241 is moved to a position higher than the second support member 242, the table 1 is caused to pitch such that its X1 side becomes higher. Also, as the first support member 241 and the second support member 242 are moved to the same height position, the table 1 is caused to pitch into a horizontal posture.

As illustrated in FIG. 13, in a view of the table 1 from the Y direction, the articulated robotic arm 2 is capable of causing the table 1 to pitch up to an angle θ2 clockwise with respect to the horizontal direction and causing the table 1 to pitch up to the angle θ2 counterclockwise with respect to the horizontal direction. θ2 is 15 degrees, for example.

The control unit 3 is installed inside the base 21 and controls the movement of the table 1 by the articulated robotic arm 2. Specifically, the control unit 3 moves the table 1 by controlling the drive of the articulated robotic arm 2 based on an operation by a medical person (operator).

The radiographic imaging apparatus 300 is capable of capturing a radiographic projection image of the patient 10 placed on the table 1. The X-ray irradiation part 301 and the X-ray detection part 302 are supported on the C-arm 303. The X-ray irradiation part 301 and the X-ray detection part 302 are moved with movement of the C-arm 303, and are positioned to face each other during radiography from opposite sides of an imaging site in the patient 10. For example, one of the X-ray irradiation part 301 and the X-ray detection part 302 is positioned in a space above the table 1 while the other is positioned in a space under the table 1. Also, during radiography, the C-arm 303, supporting the X-ray irradiation part 301 and the X-ray detection part 302, is positioned in the spaces above and under the table 1 as well.

As illustrated in FIG. 1, the X-ray irradiation part 301 is disposed to face the X-ray detection part 302. Also, the X-ray irradiation part 301 is capable of emitting X rays toward the X-ray detection part 302. The X-ray detection part 302 detects the X rays emitted by the X-ray irradiation part 301. The X-ray detection part 302 includes a flat panel detector (FPD). The X-ray detection part 302 captures a radiographic image based on the detected X rays. Specifically, the X-ray detection part 302 converts the detected X rays into electric signals and transmits them to an image processing unit (not illustrated).

The X-ray irradiation part 301 is connected to one end of the C-arm 303, and the X-ray detection part 302 is connected to the opposite end of the C-arm 303. The C-arm 303 has a substantially C-shape. In this way, the C-arm 303 can support the X-ray irradiation part 301 and the X-ray detection part 302 while extending around the table 1 and the patient 10 to avoid interfering with them during radiography. The C-arm 303 is capable of moving relative to the table 1. Specifically, the C-arm 303 is capable of moving horizontally and vertically and also rotating about a horizontal rotation axis and a vertical rotation axis to position the X-ray irradiation part 301 and the X-ray detection part 302 to desired positions relative to the patient 10 placed on the table 1. The C-arm 303 is moved by a drive part (not illustrated) based on an operation by a medical person (operator). The C-arm 303 is also manually movable by a medical person (operator).

Advantageous Effects of this Embodiment

This embodiment can offer the following advantageous effects.

In this embodiment, as explained above, the articulated robotic arm 2 is capable of assuming the first posture, in which its length in the direction parallel to the longitudinal direction of the table 1 (X direction) is shorter than or equal to ½ of the length of the table 1 in the longitudinal direction. In this way, a space covering ½ or more of the table 1 in the longitudinal direction can be left under the opposite side (X1 direction side) of the table 1 from the one end side thereof, which is supported by the articulated robotic arm 2. Accordingly, a sufficient space can be left under and around the table 1, on which to place a patient. Consequently, the C-arm 303, to which the X-ray irradiation part 301 and the X-ray detection part 302 are connected, can be placed under the table 1, and also the freedom in access to the table 1 by medical personnel such as surgeons, assistants, nurses, and medical technicians can be enhanced.

Also, in this embodiment, as explained above, the articulated robotic arm 2 in the first posture is disposed within the space between the opposite transverse ends of the table 1 in the direction parallel to the transverse direction of the table 1 (Y direction) in the plan view (as seen from the Z direction). the portion of the articulated robotic arm 2 sticking out from the table 1 has a length in the direction parallel to the transverse direction of the table 1 (Y direction) that is shorter than or equal to the length of the table 1 in the transverse direction. Thus, with the articulated robotic arm 2 set in the first posture, the articulated robotic arm 2 does not stick out in the transverse direction of the table 1. In this way, it is possible to effectively prevent interference of the articulated robotic arm 2 with medical personnel and other equipment.

Also, in this embodiment, as explained above, the articulated robotic arm 2 is capable of assuming the second posture, which is different from the first posture in the plan view (as seen from the Z direction). Moreover, the length of the articulated robotic arm 2 in the second posture in the direction parallel to the longitudinal direction of the table 1 (X direction) is shorter than or equal to ½ of the length of the table 1 in the longitudinal direction, and the portion of the articulated robotic arm 2 in the second posture sticking out from the table 1 has a length in the direction parallel to the transverse direction of the table 1 (Y direction) that is shorter than or equal to the length of the table 1 in the transverse direction. In this way, it is possible to prevent the articulated robotic arm 2 from greatly sticking out in the transverse direction of the table 1 and therefore prevent interference of the articulated robotic arm 2 with medical personnel and other equipment. It is also possible to, for example, set the first posture as an imaging position and the second posture as a surgical operation position or set the first posture as a surgical operation position and the second posture as an imaging position. This can enhance the freedom in usage of the operating room.

Also, in this embodiment, as explained above, the articulated robotic arm 2 in the first posture is disposed to be entirely hidden under the table 1 in the plan view (as seen from the Z direction). In this way, the articulated robotic arm 2 does not stick out from the table 1 in the plan view. Hence, it is possible to more effectively prevent interference of the articulated robotic arm 2 with medical personnel while medical practice such as a surgical operation is performed.

Also, in this embodiment, as explained above, the articulated robotic arm 2 is provided with the horizontal articulated assembly 22, including the horizontal joints 221, 222, and 223, and the vertical articulated assembly 23, including the vertical joints 231, 232, and 233. Thus, the table 1 can be easily moved to a desired position in the horizontal direction by the horizontal articulated assembly 22, including the horizontal joints 221, 222, and 223. Moreover, the table 1 can be easily moved to a desired position in the vertical direction (Z direction) by the vertical articulated assembly 23, including the vertical joints 231, 232, and 233.

Also, in this embodiment, as explained above, the horizontal articulated assembly 22 is provided with the three horizontal joints 221, 222, and 223. Thus, considering that the horizontal articulated assembly 22 has a certain length when fully extended, the horizontal articulated assembly 22 can have short joint-to-joint distances and therefore be compact when folded and shortened as compared to a case where it is provided with one or two horizontal joints. Moreover, the horizontal articulated assembly 22 can simplify the apparatus configuration as compared to a case where it is provided with four or more horizontal joints. The vertical articulated assembly 23 is provided with the three horizontal joints 231, 232, and 233. Thus, considering that the vertical articulated assembly 23 has a certain length when fully extended, the vertical articulated assembly 23 can have short joint-to-joint distances and therefore be compact when folded and shortened as compared to a case where it is provided with one or two vertical joints. Moreover, the vertical articulated assembly 23 can simplify the apparatus configuration as compared to a case where it is provided with four or more vertical joints.

Also, in this embodiment, as explained above, the articulated robotic arm 2 causes the table 1 to yaw about an axis along the vertical direction (Z direction) by using at least one of the horizontal joints (at least one of 221, 222, and 223). Thus, the table 1 can be easily caused to yaw to a desired position by using one or more horizontal joints of the articulated robotic arm 2.

Also, in this embodiment, as explained above, the articulated robotic arm 2 translationally moves the table 1 from the first posture while maintaining its length in the direction parallel to the transverse direction of the table 1 (Y direction). In this way, the articulated robotic arm 2 can be prevented from sticking out in the transverse direction of the table 1 while moving the table 1 in the horizontal direction. This makes it possible to prevent interference of the articulated robotic arm 2 with medical personnel situated on a side of the table 1 in the transverse direction while moving the table 1.

Also, in this embodiment, as explained above, the articulated robotic arm 2 moves the table 1 in the vertical direction (Z direction) by using the vertical articulated assembly 23 while maintaining the first posture. In this way, the articulated robotic arm 2 can be prevented from sticking out in the horizontal direction while moving the table 1 in the vertical direction. This makes it possible to prevent interference of the articulated robotic arm 2 with medical personnel situated on a side of the table 1 while moving the table 1.

Also, in this embodiment, as explained above, the articulated robotic arm 2 causes the table 1 to roll about an axis along the longitudinal direction (X direction) by using at least one of the vertical joints (at least one of 231, 232, and 233). Thus, the table 1 can be easily caused to roll to a desired rotation angle position by using one or more vertical joints of the articulated robotic arm 2.

Also, in this embodiment, as explained above, the articulated robotic arm 2 is provided with the pitch mechanism 24, which supports the table 1 and causes the table 1 to pitch about an axis along the transverse direction (Y direction). Moreover, the pitch mechanism 24 is provided with the first ball screw 243, which is disposed such that its shaft extends in the vertical direction (Z direction), the second ball screw 244, which is disposed such that its shaft extends in the vertical direction, the first support member 241, which supports the table 1 and is moved in the vertical direction by the first ball screw 243 and, and the second support member 242, which supports the table 1 and is moved in the vertical direction by the second ball screw 244. Furthermore, the first support member 241 and the second support member 242 are disposed away from each other by a predetermined distance in the direction parallel to the longitudinal direction of the table 1 (X direction). In this way, the table 1 can be easily caused to pitch to a desired rotation angle position by driving the first ball screw 243 and the second ball screw 244 in conjunction with each other.

Also, in this embodiment, as explained above, the pitch mechanism 24 is provided with the first linear guide 245, which is disposed to extend in the direction parallel to the direction of extension of the first ball screw 243, and the second linear guide 246, which is disposed to extend in the direction parallel to the direction of extension of the second ball screw 244. Moreover, the first support member 241 is slidably mounted on the first linear guide 245, and the second support member 242 is slidably mounted on the second linear guide 246. In this way, the first linear guide 245 allows accurate linear movement of the first support member 241, and the second linear guide 246 allows accurate linear movement of the second support member 242. Hence, the table 1 can be caused to pitch accurately.

Also, in this embodiment, as explained above, the one end of the horizontal articulated assembly 22 is supported on the base 21 while the opposite end of the horizontal articulated assembly 22 supports the one end of the vertical articulated assembly 23, and the pitch mechanism 24 is supported on the opposite end of the vertical articulated assembly 23. Thus, the horizontal joints 221, 222, and 223 can be disposed together on the base 21 side, and the vertical joints 231, 232, and 233 can be disposed together on the table 1 side. Then, the table 1 can be moved in the horizontal direction by driving the horizontal joints 221, 222, and 223 on the base 21 side, and the table 1 can be moved in the vertical direction (Z direction) by driving the vertical joints 231, 232, and 233 on the table 1 side. In this way, the horizontal joints 221, 222, and 223 and the vertical joints 231, 232, and 233 do not need to be driven in conjunction with each other to move the table 1 in the horizontal direction or in the vertical direction. Accordingly, the control of drive of the articulated robotic arm 2 is less complicated than when the vertical joints and the horizontal joints are disposed alternately. Moreover, since the pitch mechanism 24 can be provided on the table 1 side of the vertical articulated assembly 23, the table 1 can be easily caused to pitch by using the pitch mechanism 24 independently of the vertical articulated assembly 23.

Also, in this embodiment, as explained above, the table 1 is provided with the radiolucent part 11 and the support part 12, which is smaller in radiolucency than the radiolucent part 11, and the opposite end of the articulated robotic arm 2 supports the support part 12 on the one end side of the table 1. Thus, a sufficient space can be left under the radiolucent part 11 of the table 1 by disposing the articulated robotic arm 2 on the support part 12 side in the first posture. In this way, the radiographic imaging apparatus 300 can be easily placed under the radiolucent part 11 and capture a radiographic image.

(Modifications)

Note that the embodiment disclosed this time should be considered exemplary in all aspects and not limiting. The scope of the present invention is indicated by the claims rather than the explanation of the above embodiment and also embraces all changes that come within the meaning and range of equivalents of the claims.

For example, although the example with the configuration in which a radiographic imaging apparatus is provided in the hybrid operating system has been presented in the above embodiment, the present invention is not limited to this example. In the present invention, a magnetic resonance imaging apparatus that captures a magnetic resonance image of a patient may be provided in the hybrid operating system. Note that both a radiographic imaging apparatus and a magnetic resonance imaging apparatus may be provided in the hybrid operating system.

Also, although the example with the configuration in which a single radiographic imaging apparatus is provided in the hybrid operating system has been presented in the above embodiment, the present invention is not limited to this example. In the present invention, multiple radiographic imaging apparatuses may be provided in the hybrid operating system.

Also, although the example with the configuration in which the horizontal articulated assembly includes three horizontal joints has been presented in the above embodiment, the present invention is not limited to this example. In the present invention, the horizontal articulated assembly may include two horizontal joints or include four or more horizontal joints.

Also, although the example with the configuration in which the vertical articulated assembly includes three vertical joints has been presented in the above embodiment, the present invention is not limited to this example. In the present invention, the vertical articulated assembly may include two vertical joints or include four or more vertical joints.

Also, although the example with the configuration in which the articulated robotic arm has seven degrees of freedom has been presented in the above embodiment, the present invention is not limited to this example. In the present invention, the robotic arm may have six or fewer degrees of freedom or have eight or more degrees of freedom.

Also, although the example with a C-arm radiographic imaging apparatus including an X-ray irradiation part and an X-ray detection part supported on a C-arm has been presented in the above embodiment, the present invention is not limited to this example. In the present invention, for example, the radiographic imaging apparatus may include an X-ray irradiation part and an X-ray detection part disposed and supported to face each other in the vertical direction.

Also, although the example with the configuration in which the base is buried in and fixed to the floor has been presented in the above embodiment, the present invention is not limited to this example. In the present invention, the base may be fixed to the surface of the floor.

Also, although the example with the configuration in which the horizontal joints 221 to 223 and the vertical joints 231 to 233 each include a servomotor, a reducer, and an electromagnetic brake has been presented in the above embodiment, the present invention is not limited to this example. In the present invention, each joint may include a servomotor incorporating a first electromagnetic brake, a second electromagnetic brake mounted to the rotation shaft of the servomotor, a first reducer, and a second reducer. The horizontal joints 221 to 223 and the vertical joints 231 to 233 may each be rotated about the corresponding rotation axis by driving the servomotor.

The above-described aspects may be combined with each other as practicable within the contemplated scope of embodiments. The above described embodiments are to be considered in all respects as illustrative, and not restrictive. The illustrated and described embodiments may be extended to encompass other embodiments in addition to those specifically described above without departing from the intended scope of the invention. The scope of the invention is to be determined by the appended claims when read in light of the specification including equivalents, rather than solely by the foregoing description. Thus, all configurations including configurations that fall within equivalent arrangements of the claims are intended to be embraced in the invention.

The invention claimed is:

1. An operating table comprising:
a table including a radiolucent part on which to place a patient and a support part made of a material having a radiolucency smaller than that of the radiolucent part;
a base buried or fixed to a floor; and
an articulated robotic arm including a first end supported on the base and a second end supporting the support part of the table at a position near a first end in a longitudinal direction of the table, wherein
the robotic arm includes a horizontal articulated assembly including horizontal joints and a vertical articulated assembly including vertical joints, the horizontal articulated assembly provided between the base and the vertical articulated assembly, and the vertical articulated assembly provided between the horizontal articulated assembly and the table,
a distance between each pair of adjacent joints among the horizontal joints and the vertical joints is shorter than a length of the table in a transverse direction of the table, such that an entirety of the vertical articulated assembly is hidden under the table in a plan view in any posture of the robotic arm, wherein the robotic arm is configured, when the table is situated at a predetermined position, to take a first posture in which a length of the robotic arm in the longitudinal direction of the table is shorter than or equal to ½ of a length of the table in the longitudinal direction of the table in the plan view and the entire robotic arm is hidden under the support part of the table in the plan view.

2. The operating table according to claim 1, wherein in the first posture, a length of the robotic arm in the transverse direction of the table is shorter than or equal to the length of the table in the transverse direction of the table.

3. The operating table according to claim 1, wherein
the robotic arm is configured to take a second posture different from the first posture when the table is situated at a second predetermined position horizontally different from the predetermined position, and
in the second posture, the length of the robotic arm in the longitudinal direction of the table is shorter than or equal to ½ of the length of the table in the longitudinal direction of the table, and in the second posture, a portion of the robotic arm sticking out from the table has a length in the transverse direction of the table that is shorter than or equal to the length of the table in the transverse direction of the table.

4. The operating table according to claim 1, wherein the robotic arm includes at least six joints.

5. The operating table according to claim 1, wherein each of the horizontal joints is rotatable about an axis along a vertical direction and each of the vertical joints is rotatable about an axis along a horizontal direction.

6. The operating table according to claim 5, wherein the horizontal articulated assembly includes three horizontal joints, and the vertical articulated assembly includes three vertical joints.

7. The operating table according to claim 5, wherein the articulated robotic arm is configured to cause the table to yaw about the axis along the vertical direction by using at least one of the horizontal joints.

8. The operating table according to claim 5, wherein the robotic arm is configured to move the table in the vertical direction by using the vertical articulated assembly while maintaining the first posture.

9. The operating table according to claim 5, wherein the articulated robotic arm is configured to cause the table to roll about an axis along the longitudinal direction of the table by using at least one of the vertical joints.

10. The operating table according to claim 1, wherein the robotic arm is configured to translationally move the table in the longitudinal direction of the table along a horizontal direction from the predetermined position without any part of the robotic arm sticking out from the table in the transverse direction of the table in the plan view.

11. The operating table according to claim 1, wherein the robotic arm includes a pitch mechanism that supports the table and configured to cause the table to pitch about an axis along the transverse direction of the table to incline the longitudinal direction of the table with respect to a horizontal direction.

12. The operating table according to claim 11, wherein
a first end of the horizontal articulated assembly is supported on the base and a second end of the horizontal articulated assembly supports a first end of the vertical articulated assembly, and
the pitch mechanism is supported on a second end of the vertical articulated assembly and the pitch mechanism that supports the table and is configured to cause the table to pitch about the axis along the transverse direction of the table to incline the longitudinal direction of the table with respect to the horizontal direction.

13. The operating table according to claim 1, wherein the robotic arm is supported on the base such that the robotic arm is rotatable about an axis along a vertical direction.

14. A hybrid operating system comprising:
at least one imaging apparatus selected from a radiographic imaging apparatus that captures a radiographic projection image and a magnetic resonance imaging apparatus that captures a magnetic resonance image; and
the operating table according to claim 1.

15. The operating table according to claim 1, wherein
the robotic arm is configured to translationally move the table along a horizontal direction from the predetermined position while maintaining a length of the robotic arm in the transverse direction of the table.

16. The operating table according to claim 1, wherein
the robotic arm is configured, when the table is situated at the predetermined position, to take the first posture in which the length of the robotic arm in the longitudinal direction of the table is shorter than or equal to ½ of the length of the table in the longitudinal direction in the plan view and the entire robotic arm and the base are hidden under the support part of the table in the plan view.

17. The operating table according to claim 1, wherein
the robotic arm is configured to translationally move the table relative to the base in the longitudinal direction by the horizontal articulated assembly, while maintaining a length of the robotic arm in the transverse direction and while maintaining the robotic arm remaining between opposite ends of the table in the transverse direction.

18. The operating table according to claim 1, wherein
lengths of the radiolucent part and the support part of the table in the transverse direction of the table are longer than or equal to 500 mm and shorter than or equal to 800 mm.

* * * * *